US009386997B2

(12) United States Patent
McCarthy et al.

(10) Patent No.: US 9,386,997 B2
(45) Date of Patent: Jul. 12, 2016

(54) TUNNEL GAGE

(71) Applicant: Smith & Nephew, Inc., Memphis, TN (US)

(72) Inventors: Gary Robert McCarthy, East Bridgewater, MA (US); Susan L Spear, Pawtucket, RI (US); Deborah A Leahy, Reading, MA (US)

(73) Assignee: Smith & Nephew, Inc., Memphis, TN (US)

( * ) Notice: Subject to any disclaimer, the term of this patent is extended or adjusted under 35 U.S.C. 154(b) by 83 days.

(21) Appl. No.: 13/853,179

(22) Filed: Mar. 29, 2013

(65) Prior Publication Data

US 2014/0296861 A1   Oct. 2, 2014

(51) Int. Cl.
*A61B 17/17* (2006.01)
*A61B 5/107* (2006.01)
*A61F 2/08* (2006.01)
*A61B 17/16* (2006.01)

(52) U.S. Cl.
CPC .......... *A61B 17/1714* (2013.01); *A61B 5/1076* (2013.01); *A61B 17/16* (2013.01); *A61F 2/0805* (2013.01)

(58) Field of Classification Search
CPC ............ A61B 5/1076; A61B 17/1714; A61B 2019/462
USPC ........... 606/86 R, 87, 88, 96, 102, 104; 7/164
See application file for complete search history.

(56) References Cited

U.S. PATENT DOCUMENTS

| 5,071,420 A | 12/1991 | Paulos et al. | |
| 5,122,146 A | 6/1992 | Chapman et al. | |
| 5,139,520 A | 8/1992 | Rosenberg | |
| 5,180,388 A * | 1/1993 | DiCarlo | 606/60 |
| 5,403,321 A * | 4/1995 | DiMarco | 606/96 |
| 5,549,613 A | 8/1996 | Goble et al. | |
| 5,645,588 A | 7/1997 | Graf et al. | |
| 5,928,243 A * | 7/1999 | Guyer | 606/102 |
| 5,931,840 A | 8/1999 | Goble et al. | |
| 6,547,795 B2 * | 4/2003 | Schneiderman | 606/96 |
| 7,172,599 B2 * | 2/2007 | Steffensmeier et al. | 606/102 |
| 8,734,461 B2 * | 5/2014 | Ellis et al. | 606/96 |

(Continued)

FOREIGN PATENT DOCUMENTS

| CN | 2719254 | 8/2005 |
| DE | 4016476 A1 | 11/1991 |

(Continued)

OTHER PUBLICATIONS

Search Report, PCT/US2014/031827, Jun. 24, 2014, pp. 6.

(Continued)

*Primary Examiner* — Christian Sevilla
*Assistant Examiner* — Eric S Gibson
(74) *Attorney, Agent, or Firm* — Burns & Levinson LLP; Joseph M. Maraia

(57) ABSTRACT

In one embodiment, a device for measuring a length of a bone tunnel is provided. The device includes: a gauge comprising an annular shaft coupled to a handle, the handle including a constrained channel configured for receiving a passing pin from the annular shaft and displaying the passing pin in relation to a scale. In another embodiment, a method for measuring length of the bone tunnel is provided. A method and another device are provided.

16 Claims, 4 Drawing Sheets

(56) References Cited

U.S. PATENT DOCUMENTS

| | | |
|---|---|---|
| 2002/0133165 A1 | 9/2002 | Whittaker et al. |
| 2003/0032865 A1 | 2/2003 | Estes et al. |
| 2004/0092936 A1 | 5/2004 | Miller et al. |
| 2005/0085825 A1* | 4/2005 | Castaneda ............ 606/102 |
| 2005/0187560 A1 | 8/2005 | Dietzel et al. |
| 2008/0262555 A1 | 10/2008 | Assell et al. |
| 2009/0022801 A1 | 1/2009 | Vachon |
| 2009/0228015 A1 | 9/2009 | Ellis et al. |
| 2009/0306675 A1 | 12/2009 | Wong et al. |
| 2010/0145340 A1* | 6/2010 | Phan et al. ............ 606/79 |
| 2010/0198227 A1* | 8/2010 | Kim ............ A61B 5/1076 606/102 |
| 2011/0166607 A1* | 7/2011 | Castaneda et al. ......... 606/291 |
| 2012/0109132 A1* | 5/2012 | Ellis et al. ............ 606/80 |
| 2012/0330323 A1* | 12/2012 | Lizardi et al. .......... 606/102 |
| 2013/0096566 A1* | 4/2013 | Bowen et al. .......... 606/102 |
| 2013/0110120 A1* | 5/2013 | Baroud et al. .......... 606/102 |
| 2014/0276884 A1* | 9/2014 | Lizardi et al. .......... 606/102 |
| 2014/0296861 A1* | 10/2014 | McCarthy et al. ......... 606/96 |

FOREIGN PATENT DOCUMENTS

| | | |
|---|---|---|
| EP | 0361756 A1 | 4/1990 |
| EP | 0556570 A1 | 8/1993 |
| EP | 2008585 A1 | 12/2008 |
| FR | 636 447 A | 4/1928 |
| FR | 2901465 A1 | 11/2007 |
| WO | 9415556 A1 | 7/1994 |
| WO | 2005122921 A2 | 12/2005 |
| WO | WO 2008/091690 A1 | 7/2008 |

OTHER PUBLICATIONS

International Preliminary Report for related International Application No. PCT/US2014/031827 issued Sep. 29, 2015.
Notice of Reasons for Rejection for Japanese Patent Application No. 2013-500209 mailed Jul. 13, 2015.
International Preliminary Report of Patentability for International Application No. PCT/US2011/028844, mailed Sep. 27, 2012.
First Office Action from related Chinese Application No. 201180014463.5, dated Jul. 8, 2014.
Patent Examination Report from related Australian Patent Application No. 2011227190 dated Mar. 25, 2015.

* cited by examiner

TUNNEL GAGE

BACKGROUND

1. Field

The invention disclosed herein relates to a device for use in ligament reconstruction surgery, and more specifically, a device and method for performing measurements.

2. Description of the Related Art

Common techniques for reconstruction of ligaments require the drilling of a tunnel through bone. For example, reconstruction of a torn anterior cruciate ligament (ACL) requires drilling through the femur of a patient. Once a femoral tunnel has been drilled, a surgeon needs to perform measurements to determine the depth of the tunnel to aide in selection of the appropriate repair technique.

While a variety of devices are available to measure the length of the femoral tunnel, many of these devices are complicated to use and may lead to confusion during surgical procedures. For example, some devices make use of a guide wire that is passed into the femoral tunnel and received by a measuring device as it exits the femoral tunnel. Unfortunately, the various receiving devices presently available often do not securely retain the guide wire. Accordingly, this may lead to erroneous measurements, and worse yet to glove damage or laceration of the surgeon.

Thus, what are needed are methods and apparatus to provide for accurate and safe measurement of the femoral tunnel. Preferably, the methods and apparatus are simple and easy to understand during a surgical procedure as well as cost-effective.

SUMMARY

In one embodiment, a device for measuring a length of a bone tunnel is provided. The device includes: a gauge comprising an annular shaft coupled to a handle, the handle including a constrained channel configured for receiving a passing pin from the annular shaft and displaying the passing pin in relation to a scale.

In another embodiment, a method for measuring length of the bone tunnel is provided. The method includes: placing a gauge over a passing pin, the tunnel gauge including an annular shaft coupled to a handle, the handle also having a constrained channel configured for receiving the passing pin from the annular shaft and displaying the passing pin in relation to a scale; and, comparing a reference mark on the passing pin to the gauge to determine the length.

In a further embodiment, a device for measuring a length of a bone tunnel is provided. The device includes: a passing pin having a region configured to be maintained within a constrained channel of a measurement device; and, a gauge including an annular shaft coupled to a handle, the handle also having a constrained channel configured for receiving the passing pin from the annular shaft and displaying the passing pin in relation to a scale.

BRIEF DESCRIPTION OF THE DRAWINGS

The features and advantages of the invention are apparent from the following description taken in conjunction with the accompanying drawings in which:

FIG. 3A provides the isometric view of a complete embodiment of the handle, while FIG. 3B provides a cutaway of the isometric view of FIG. 3A. FIG. 3C provides a close-up view of the cutaway shown in FIG. 3B, additionally with a cross-section of the passing pin;

DETAILED DESCRIPTION

Disclosed herein are methods and apparatus for performing measurements of a bone tunnel. As discussed herein, the bone tunnel is a femoral tunnel (i.e., a hole that has been drilled through a portion of a femur of a patient). However, this is merely exemplary and it is not limiting of the teachings herein.

Generally, the apparatus disclosed herein is a two-part apparatus. In order to measure the femoral tunnel, a first part, a passing pin, is inserted into the femoral tunnel. Insertion of the passing pin is stopped when a reference mark on the passing pin aligns with an outer surface of the femoral condyle. A second part of the device, a tunnel gauge, is then disposed over a portion of the passing pin that has emerged from an opposing side of the femur. By placing the tunnel gauge against the opposing side of the femoral condyle and by referencing a scale on the tunnel gauge, a surgeon is able to determine a depth of the femoral tunnel.

Figure 1:
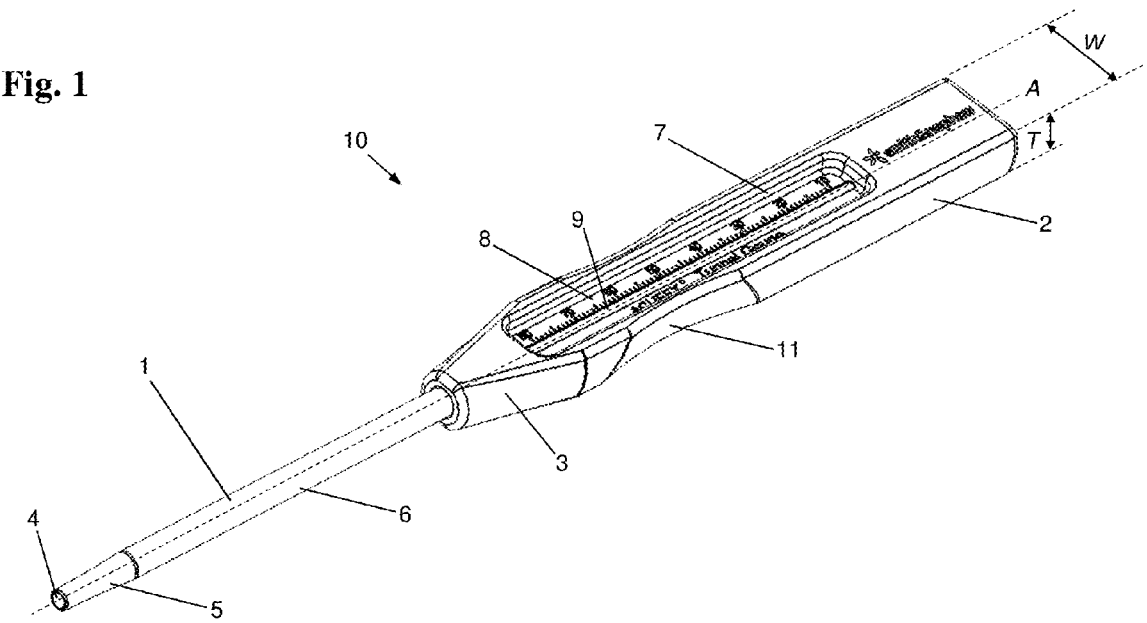
FIG. 1 is an isometric view of a tunnel gauge according to an embodiment of the invention.

Referring now to FIG. 1, there is shown an exemplary tunnel gauge 10 according to the teachings herein. In this example, the tunnel gauge 10 includes a shaft 1 and a handle 2. Generally, the shaft 1 is mounted to the handle 2 at a base 3.

Note that merely for convenience of referencing and an explanation of the teachings herein, the terms "distal" and "proximal" as well as other such relational or descriptive terms are used. This terminology should not be construed to imply any orientation for implementation of the methods and apparatus disclosed herein. Generally, the term "distal" and "proximal" are with respect to an individual using the device (e.g., a physician). For example, when inserting a passing pin, an end of the passing pin that is being inserted may be referred to as a "distal" end of the passing pin. Similarly, when placing the tunnel gauge 10 against the femur, it may be considered that the shaft 1 is a distal portion of the tunnel gauge 10, while the handle 2 is a proximal portion of the tunnel gauge 10.

In the exemplary embodiment, the tunnel gauge 10 is disposed about a longitudinal axis, A. Again, the longitudinal axis, A, and any other techniques for referencing are merely for purposes of explanation and are not limiting of the teachings herein.

In the embodiment shown, the shaft 1 is an annular cylinder. The shaft 1 includes a receiver 4, a tapered section 5, and an elongated section 6. The shaft 1 may be mounted to the handle 2 at the body 3 by any one (or more) of a variety of suitable techniques. For example, the shaft 1 may be threaded into a receiving section within the body 3. The shaft 1 may be glued, hot melted, fastened or otherwise mated or joined with the body 3.

Figure 4:
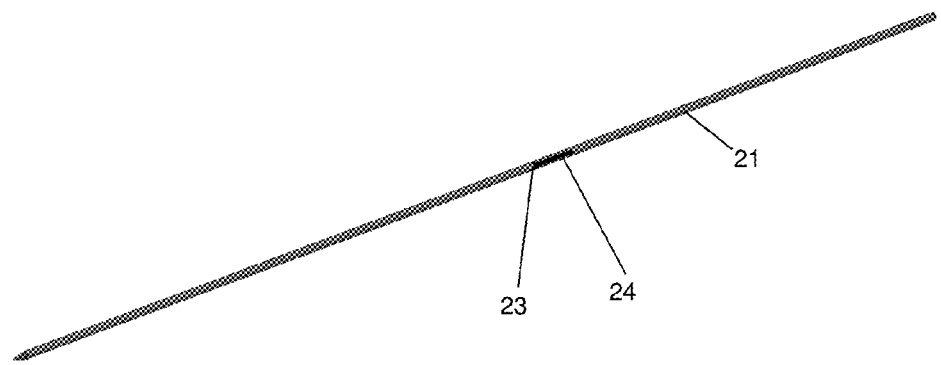
FIG. 4 provides an isometric view of a passing pin suited for use with the tunnel gauge of FIG. 1.

Generally, the shaft 1 has an inner diameter designed to accommodate a passing pin (as shown in FIG. 4, and as discussed further herein). For example, the shaft 1 may have an inner diameter that is slightly larger than 2.4 mm or 2.7 mm, such that it may securely accommodate passage of the 2.4 mm or 2.7 mm passing pin, respectively.

In the embodiment shown, the shaft 1 is an annular cylinder. The shaft 1 includes a receiver 4, a tapered section 5, and an elongated section 6. The shaft 1 may be mounted to the handle 2 at the base 3 by any one (or more) of a variety of suitable techniques. For example, the shaft 1 may be threaded into a receiving section within the base 3. The shaft 1 may be glued, hot melted, fastened or otherwise mated or joined with the base 3.

The handle 2 includes a central channel 9. The channel 9 is configured to receive the passing pin as it emerges from the elongated section 6 of the shaft 1. In order to view the central channel 9 (and therefore the passing pin), a window 7 is provided within the body of the handle 2. In this example, the window 7 presents as a cutaway along a length of the handle 2.

Disposed within the window 7 is at least one gauge 8. The gauge 8 is disposed along a length of the channel 9 within the window 7. Accordingly, as the passing pin is received within the channel 9, and extends into the handle 2, a depth of the femoral tunnel may be ascertained. That is, the gauge 8 includes at least one scale for measuring depth of the femoral tunnel (i.e., a length of the femoral tunnel). This will be explained in greater detail further herein.

In this example, the gauge 8 is provided in centimeters, with subdivisions of millimeters. However, any linear scale deemed appropriate may be used in the gauge 8 (i.e., system international (SI), English, metric or other standards may be used).

Figure 2:
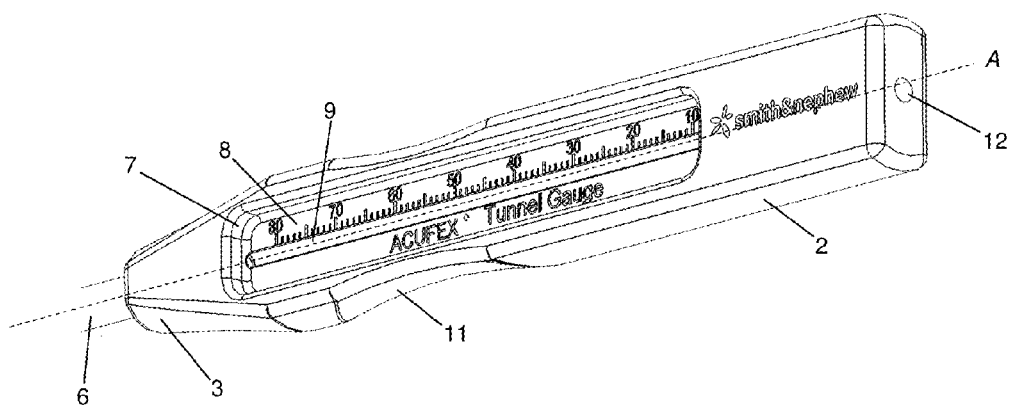
FIG. 2 is an isometric view of a handle of the tunnel gauge of FIG. 1, from a different angle.

Referring now to FIG. 2 some of the foregoing aspects are shown from another angle. In addition, it may be seen that the handle 2 may include an exit-way 12 from the channel 9. Generally, the exit-way 12 may be provided to facilitate cleaning of the handle 2 after use. For example, it may be desirable to flush a sterilizing cleaning fluid through at least one of the receiver 4 and the exit-way 12 to ensure removal of all debris as well as sterilization of the tunnel gauge 10.

Figure 3A:
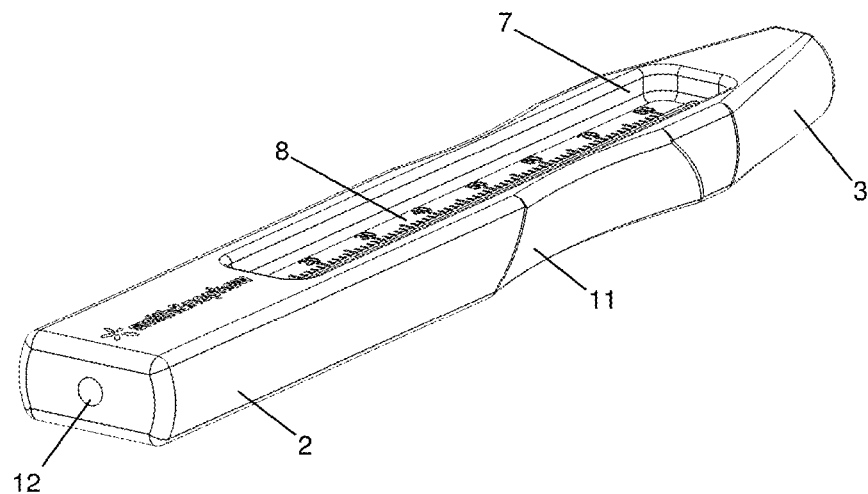
FIGS. 3A, 3B and 3C, collectively referred to herein as FIG. 3, provide another isometric view of the handle of the tunnel gauge of FIG. 1.
Figure 3B:
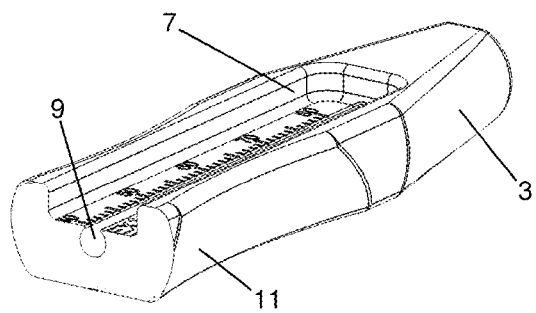

Referring to FIGS. 3A and 3B, additional isometric views of the handle 2 are shown. FIG. 3A is provided merely for understanding the depiction in FIG. 3B, which depicts a cutaway portion of the handle 2. As shown in FIG. 3B, the channel 9 may be configured with a "C" shaped cross-section. That is, the channel 9 may be configured to securely retain the passing pin while providing for display thereof. An example of this is better shown in FIG. 3C.

Figure 3C:
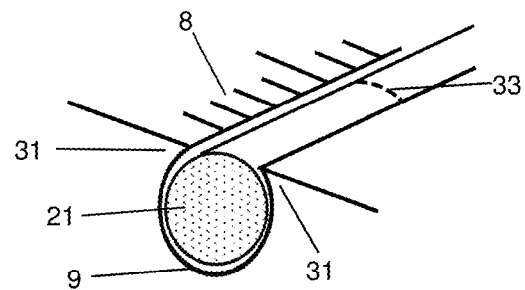

Referring now to FIG. 3C there is shown an exploded view of the cutaway portion of the channel 9 of FIG. 3B. Further, in this illustration, a portion of a passing pin 21 is shown. As may be seen in FIG. 3C, the channel 9 may include at least one section of retaining material 31. More specifically, retaining material 31 may be included to retain the passing pin 21 within the channel 9. In this example, retaining material 31 is disposed symmetrically about the channel 9. However, in some embodiments, retaining material 31 is provided on merely one side of the channel 9. In use, the retaining material 31 provides for observation of the passing pin 21 while narrowing an open portion of the channel 9 substantially enough that the passing pin 21 could not be diverted out of the channel 9 (i.e., the open portion of the channel 9 has a width that is less than a diameter or width of the passing pin 21).

In this embodiment, the retaining material 31 provides for a "constrained channel" 9. It may be considered that the term "constrained channel" generally refers to any type of channel that may be characterized as having a particular geometry (e.g., a cross-section) that provides for retention of the passing pin 21 or any other similar component (e.g., a guide wire, a drill, a drill shank, and the like).

More specifically, in this example, the passing pin 21 exhibits a cross-section of a dimension, denoted as "CS." The constrained channel 9 has a relatively narrow opening. That is, a dimension for the opening provided for display of the passing pin 21 is less than that of the cross-section of the passing pin 21. Accordingly, it should be understood that the constrained channel 9 may have a narrow opening the generally limits the capability of the passing pin to migrate from the channel 9.

Also shown in FIG. 3C, is a measuring mark 33. In this example, the measuring mark 33 is characterized as a single line disposed about a circumference (or perimeter, as the case may be) of the passing pin 21. In some embodiments, the measuring mark 33 is disposed about the passing pin 21 by use of laser etching. However, any technique for providing a measuring mark 33 that is deemed appropriate may be used.

In some embodiments (not shown), the measuring mark 33 includes a plurality of marks. For example, the measuring mark 33 may include another scale. The another scale may be compared to markings in the gauge 8.

Referring now to FIG. 4, an embodiment of the passing pin 21 is shown. In this example the passing pin 21 is a unitary device. The passing pin may be flexible, rigid or exhibit any appropriate combination of properties. The passing pin 21 may include a reference mark 23 which serves as a stop point during insertion of the passing pin 21 into the femoral tunnel. In addition, the passing pin 21 may include at least one marking indicator 24 to enhance visibility of the reference mark 23. In this example, the marking indicator 24 is an elongated stripe that extends along a portion of the length of the passing pin 21.

In some embodiments, the passing pin 21 includes a fluted end. The fluted end may be provided so that the passing pin 21 may also provide for drilling of the femoral tunnel. In this example, the passing pin 21 includes a pointed end which facilitates its insertion into the femoral tunnel, once the femoral tunnel has been drilled and the drill removed. The pointed end of the passing pin 21 allows it to penetrate any drilling debris remaining in the tunnel. In use, the passing pin 21 is inserted into the femoral tunnel until the reference mark 23 is aligned with a distal cortex of the femur.

Referring back to FIG. 1, once the passing pin 21 has been inserted, the tunnel gauge 10 is disposed over the portion of the passing pin 21 which extends from the femur, and in some instances from a skin of the patient. Once the shaft 1 of the tunnel gauge 10 has been disposed over the passing pin 21, the shaft 1 is then pushed through the surrounding tissue. Accordingly, the tapered section 5 of the shaft 1 facilitates insertion of the shaft 1 by displacing the tissue. Once the receiver 4 has been abutted against a proximal cortex of the femur, it is possible to accurately measure a depth of the femoral tunnel.

Figure 5:
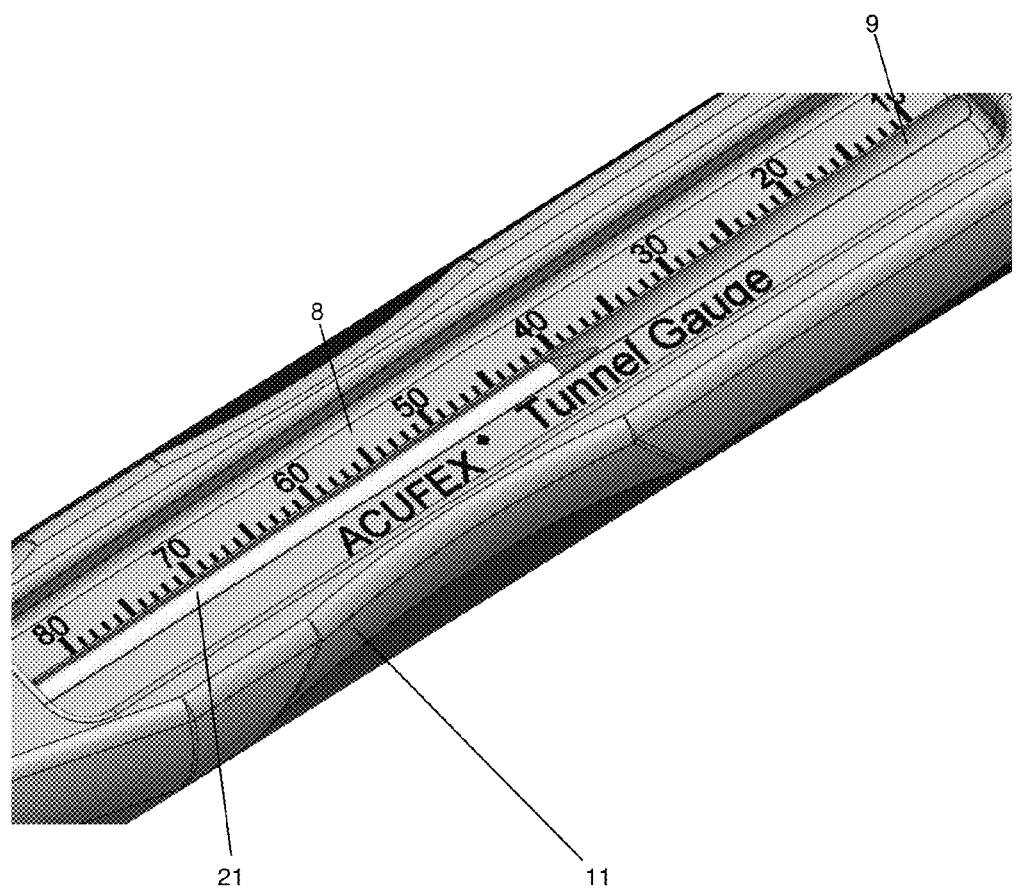
FIG. 5 is a blown up isometric view of a portion of the handle of the tunnel gauge with the passing pin loaded therein; and, FIG. 6 is an isometric cutaway view of the tunnel gauge in use with the passing pin.

Referring now to FIG. 5, an embodiment of the tunnel gauge 10 with the passing pin 21 loaded therein is shown. It may be seen that, in this example, the femoral tunnel is about 41 mm deep.

Figure 6:
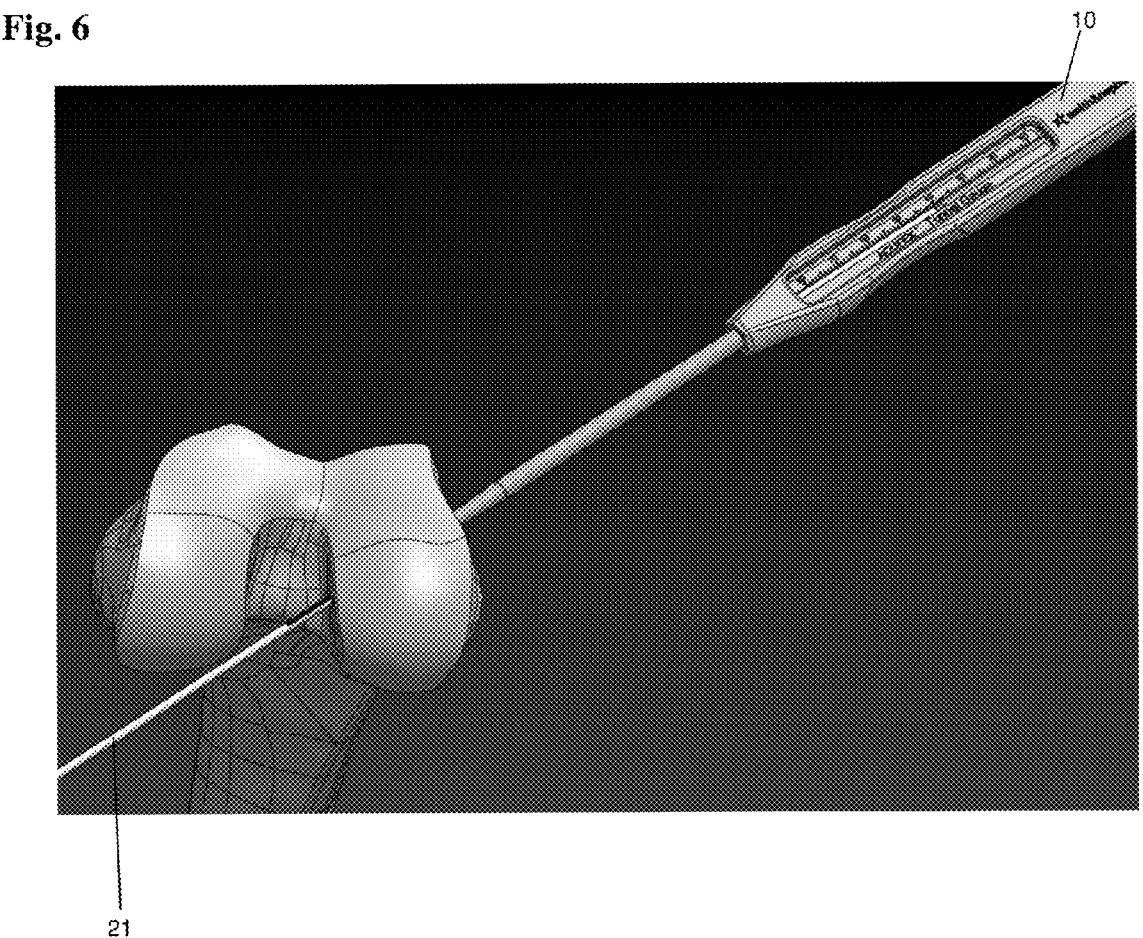

According to FIG. 6 a cutaway view of the tunnel gauge 10 and passing pin 21 is shown in use. All surrounding tissue has been removed from this illustration to better depict cooperation of the passing pin 21 with the tunnel gauge 10.

Having thus introduced embodiments of the tunnel gauge 10, some additional aspects are now provided.

In some embodiments, the handle 2 and the shaft 1 are a unitary structure. For example, the handle 2 and the shaft 1 may be fabricated from a biocompatible plastic. This may be performed by injection molding or other suitable techniques. In some additional embodiments, one of the handle 2 and the shaft 1 is fabricated from a plastic or polymeric material while the other component is fabricated from metal or a metallic material. One exemplary polymeric material is polyphenylsulfone (PPSU). PPSU may be characterized as a material having a high heat resistance and excellent hydrolytic stability. Other materials that may withstand repeated cycling through sterilization environment (i.e., cleaning with steam, alcohol or other suitable materials) and that provide desired structural integrity may be used.

The passing pin 21 may be provided in a variety of configurations. For example, the passing pin 21 may be generally cylindrical (such as in the form of a wire), may be annular (such as in the form of a straw), or of another cross-sectional geometry (such as a square, a rectangle, a triangle, or an n-gon) as deemed appropriate and suited for use with the constrained channel 9. The passing pin 21 may include at least one loop or eyelet, such as for carrying suture. Although discussed herein as the passing pin 21, any device suited for insertion through the femoral tunnel (or any other bone tunnel) may be used with the tunnel gauge 10. For example, the tunnel gauge 10 may be configured to receive a drill.

In some embodiments, the handle 2 may be separated from the shaft 1 to facilitate cleaning and sterilization of the tunnel gauge 10.

Although presented herein with regards to reconstruction of ligaments and drilling of a femoral tunnel, the tunnel gauge 10 may be used to ascertain a depth or length of any type of bone tunnel, as deemed appropriate.

While the invention has been described with reference to exemplary embodiments, it will be understood by those skilled in the art that various changes may be made and equivalents may be substituted for elements thereof without departing from the scope of the invention. Therefore, it is intended that the invention not be limited to the particular embodiment disclosed as the best mode contemplated for carrying out this invention, but that the invention will include all embodiments falling within the scope of the appended claims.

What is claimed is:

1. A gauge for measuring a length of a bone tunnel, the gauge comprising:
    an annular shaft having an inner diameter and coupled to a handle, the handle comprising:
        a proximal end, a tapered distal end, and a substantially flat, elongate body extending from the proximal end to the distal end;
        a constrained channel within the handle body extending from the proximal end to the distal end, the constrained channel in direct communication with the inner diameter of the annular shaft and configured for receiving a passing pin from the inner diameter of the annular shaft, the constrained channel including at least one section of retaining material to retain the passing pin within the constrained channel; and
        a window defined by a cutaway along a length of the handle body to expose a visible length of the constrained channel, the window enabling a display of the passing pin in relation to a scale;
    wherein opposing sides of the handle body comprise bilateral depressions extending from a top surface to a bottom surface of the handle body configured for grip on the handle; and
    wherein the distal end of the handle comprises a base configured for separating from the annular shaft.

2. The gauge as in claim 1, wherein the constrained channel comprises a C-shaped cross-section.

3. The gauge as in claim 1, wherein an open portion of the constrained channel has a width which is less than a cross-sectional dimension of the passing pin.

4. The gauge as in claim 3, wherein the open portion of the constrained channel is an exit-way configured to facilitate cleaning.

5. The gauge as in claim 1, wherein the annular shaft comprises at least one of a tapered section and an elongated section.

6. The gauge as in claim 1, wherein the retaining material is disposed symmetrically about the constrained channel.

7. The gauge as in claim 1, wherein the window comprises the scale disposed along the visible length of the constrained channel.

8. The gauge as in claim 1, wherein the retaining material is disposed on one side of the constrained channel.

9. The gauge as in claim 1, wherein the inner diameter of the annular shaft is selected to be slightly larger than a cross-sectional dimension of the passing pin.

10. The gauge as in claim 9, wherein the inner diameter of the annular shaft is slightly larger than 2.4 mm or slightly larger than 2.7 mm.

11. A device for measuring a length of a bone tunnel, the device comprising:
    a gauge, the gauge comprising:
        an annular shaft having an inner diameter and coupled to a handle, the handle comprising:
        a proximal end, a tapered distal end, a substantially flat, elongate body extending from the proximal end to the distal end, and a constrained channel extending from the proximal end to the distal end, the constrained channel in direct communication with the inner diameter of the annular shaft and configured for receiving a passing pin from the inner diameter of the annular shaft, the constrained channel including at least one section of restraining material to retain the passing pin within the constrained channel; and a window to expose a visible length of the constrained channel, the window enabling a display of the passing pin in relation to a scale, wherein opposing sides of the handle comprise bilateral depressions extending from a top surface to a bottom surface of the handle;
    wherein the distal end of the handle comprises a base configured for separating from the annular shaft; and
    a passing pin that exhibits a cross-sectional area configured to be maintained within the constrained channel of the handle of the gauge, the passing pin comprising a fluted end for drilling into bone.

12. The device as in claim 11, wherein the passing pin comprises a generally circular cross-section.

13. The device as in claim 11, wherein the gauge is fabricated from at least one of a biocompatible material, a metallic material and a polymeric material.

14. The device as in claim 11, wherein the gauge is fabricated from polyphenylsulfone.

15. The device as in claim 11, wherein the retaining material is disposed symmetrically about the constrained channel.

16. The device as in claim 11, wherein the retaining material is disposed on one side of the constrained channel.

* * * * *